(12) United States Patent
Nomura et al.

(10) Patent No.: US 8,067,661 B2
(45) Date of Patent: Nov. 29, 2011

(54) METHOD FOR DECOMPOSING WATER-SOLUBLE FLUORINATED ORGANIC COMPOUND

(75) Inventors: Jumpei Nomura, Tokyo (JP); Yasuhiko Matsuoka, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/853,602

(22) Filed: Aug. 10, 2010

(65) Prior Publication Data

US 2010/0324352 A1    Dec. 23, 2010

Related U.S. Application Data

(63) Continuation of application No. PCT/JP2009/052820, filed on Feb. 18, 2009.

(30) Foreign Application Priority Data

Mar. 7, 2008   (JP) ................. 2008-057381

(51) Int. Cl.
*A62D 3/34* (2007.01)
*A62D 3/40* (2007.01)
*C01B 7/20* (2006.01)

(52) U.S. Cl. .................. 588/321; 210/915; 423/500

(58) Field of Classification Search .............. 210/763, 210/656, 750, 915; 588/316, 321; 502/327; 423/500, 245.3; *A62D 3/34*
See application file for complete search history.

(56) References Cited

U.S. PATENT DOCUMENTS 6,673,326 B1 *   1/2004   Rossin et al. .............. 423/240 S

FOREIGN PATENT DOCUMENTS

| | | | |
|---|---|---|---|
| DE | 4230553 A1 | * | 3/1994 |
| JP | 11179201 A | * | 7/1999 |
| JP | 2002-307082 | | 10/2002 |
| JP | 2002-327089 | | 11/2002 |
| JP | 2003-040805 | | 2/2003 |
| JP | 2005-154277 | | 6/2005 |
| JP | 2005-225785 | | 8/2005 |
| JP | 2006-306736 | | 11/2006 |
| JP | 2006306736 A | * | 11/2006 |

* cited by examiner

*Primary Examiner* — Stuart Hendrickson
*Assistant Examiner* — Syed Iqbal
(74) *Attorney, Agent, or Firm* — Oblon, Spivak, McClelland, Maier & Neustadt, L.L.P.

(57) ABSTRACT

To provide a good and simple method for decomposing and detoxifying a hardly decomposable fluorinated organic compound.
Specifically, a fluorinated organic compound is decomposed by bringing an aqueous solution of the fluorinated organic compound into contact with a catalyst containing a metal oxide. The metal oxide may preferably be an oxide of at least one metal selected from the group consisting of Ni, Pd, Cu, Mn, Fe and Co, and more preferably be nickel oxide. The contact temperature is preferably within the range of from 0 to 100° C. Preferably, the fluorinated organic compound to be decomposed is an organic fluorocarboxylic acid, an organic fluorosulfonic acid or a salt thereof, which is used as a surfactant or an surface treatment agent.

12 Claims, No Drawings

METHOD FOR DECOMPOSING WATER-SOLUBLE FLUORINATED ORGANIC COMPOUND

CROSS-REFERENCE TO RELATED APPLICATIONS

This application is a continuation of PCT/JP09/052820 filed Feb. 18, 2009 and claims the benefit of JP 2008-057381 filed Mar. 7, 2008.

TECHNICAL FIELD

The present invention relates to a method for decomposing a water-soluble fluorinated organic compound.

BACKGROUND ART

In recent years, the residual nature of a fluorinated organic compounds, which have been used as surfactants or surface treatment agents, in the environment has become a problem. It is reported that fluorosulfonic acids having mutagenic properties accumulate in bodies of animals including fishes, birds and humans, and there are growing concerns about their impacts on the ecosystem. With regard to fluorocarboxylic acids, their accumulating property in mammals was confirmed, and reduction of residual fluorocarboxylic acids in fluororesin articles has been promoted.

Such fluorinated organic compounds are formed from carbon-fluorine bonds having a large bond energy, so that they have high stability and they are hardly decomposable, and a high temperature of at least about 1,000° C. is required to decompose them by combustion. As decomposition methods other than combustion, photochemical decomposition (for example, Patent Documents 1 to 4) and hydrothermal decomposition (Patent Document 5) have been proposed. However, these methods require special conditions or complicated process steps, and therefore development of a more simple decomposition method has been desired.

Patent Document 1: JP-A-2002-327089
Patent Document 2: JP-A-2003-40805
Patent Document 3: JP-A-2005-154277
Patent Document 4: JP-A-2005-225785
Patent Document 5: JP-A-2006-306736

DISCLOSURE OF THE INVENTION

Object to be Accomplished by the Invention

The present invention has been accomplished to solve such problems in the conventional technology, and the object of the present invention is to provide a method for decomposing a hardly decomposable fluorinated organic compound with a simple operation.

Means to Accomplish the Object

The present invention provides a method for decomposing a fluorinated organic compound, as follows:

[1] A method for decomposing a fluorinated organic compound, comprising contacting an aqueous solution containing a water-soluble fluorinated organic compound with a catalyst containing an oxide of at least one metal selected from the group consisting of Ni, Pd, Cu, Mn, Fe and Co.

[2] The method for decomposing a fluorinated organic compound according to the above [1], wherein the metal oxide is nickel oxide.

[3] The method for decomposing a fluorinated organic compound according to the above [1] or [2], wherein the catalyst further contains, as a carrier component, at least one member selected from the group consisting of aluminum oxide, zeolite, zinc oxide, lanthanum oxide, silica, magnesium oxide, calcium oxide and titanium oxide.

[4] The method for decomposing a fluorinated organic compound according to the above [3], wherein the catalyst comprises nickel oxide and aluminum oxide, and their mass ratio (nickel oxide/aluminum oxide) is from 0.01 to 100.

[5] The method for decomposing a fluorinated organic compound according to any one of the above [1] to [4], wherein the catalyst is in the form of granules and their average size is from 0.1 μm to 1.0 cm.

[6] The method for decomposing a fluorinated organic compound according to any one of the above [1] to [4], wherein the catalyst is in the form of pellets and their average size is from 0.1 mm to 5 cm.

[7] The method for decomposing a fluorinated organic compound according to any one of the above [1] to [6], wherein the aqueous solution containing a water-soluble fluorinated organic composition is passed through a column packed with the catalyst.

[8] The method for decomposing a fluorinated organic compound according to any one of the above [1] to [7], wherein the fluorinated organic compound is a fluorocarboxylic acid, a fluorosulfonic acid or a salt thereof.

[9] The method for decomposing a fluorinated organic compound according to any one of the above [1] to [8], wherein the concentration of the fluorinated organic compound in the aqueous solution is within a range of from 1 mass ppm to 30 mass %.

[10] The method for decomposing a fluorinated organic compound according to any one of the above [1] to [9], wherein the amount of the catalyst is from 0.01 to 1,000 times the mass of the fluorinated organic compound in the aqueous solution containing the fluorinated organic compound.

[11] The method for decomposing a fluorinated organic compound according to any one of the above [1] to [10], wherein the aqueous solution containing a water-soluble fluorinated organic compound is contacted with the catalyst for a contact time of from 1 minute to 5 hours.

[12] The method for decomposing a fluorinated organic compound according to any one of the above [1] to [11], wherein the aqueous solution containing the fluorinated organic compound is contacted with the catalyst at a temperature of from 0° C. to 100° C.

EFFECTS OF THE INVENTION

By the decomposition method of the present invention, a water-soluble fluorinated organic compound, which is used as a surfactant or a surface treatment agent, can be easily decomposed. Further, in the decomposition method of the present invention, an aqueous solution containing a water-soluble fluorinated organic compound only needs to be contacted with a catalyst by means of, for example, passing through a column, and thus it is excellent in the energy efficiency as compared with the thermal decomposition at a high temperature. Therefore, the method of the present invention is effective for prevention of environmental pollution by fluorinated organic compounds.

BEST MODE FOR CARRYING OUT THE INVENTION

The catalyst used in the present invention contains, as a catalytic component, an oxide of at least one metal selected from the group consisting of Ni, Pd, Cu, Mn, Fe and Co. Among them, nickel oxide is preferred.

The amount of the metal oxide contained in the catalyst is preferably at least 1.0 mass %, more preferably at least 10 mass %, most preferably at least 20 mass %. The amount of the metal oxide may be 100 mass %.

The catalyst preferably further contains, as a carrier component which carries the metal oxide, at least one member selected from the group consisting of aluminum oxide, zeolite, zinc oxide, lanthanum oxide, silica, magnesium oxide, calcium oxide and titanium oxide. Among them, aluminum oxide is particularly preferably used.

The catalyst used in the present invention preferably comprises nickel oxide and aluminum oxide. In this case, the mixing ratio of nickel oxide and aluminum oxide i.e. nickel oxide/aluminum oxide is, in terms of mass ratio, preferably from 0.01 to 100, further preferably from 0.1 to 10.

Such a metal oxide catalyst can be produced by, for example, extruding an aqueous slurry having a carrier metal ion dissolved therein, and drying and firing it to obtain a carrier compact, followed by dipping the carrier compact in an aqueous solution having a catalytic metal ion dissolved therein, and drying and firing it.

As such a metal oxide catalyst, a commercial catalyst may be also used, and for example, a nickel oxide/aluminum oxide metal oxide catalyst manufactured by Johnson Matthey (tradename: ACCENT™ 81-1T, average particle size: 1.2 mm) is a preferred example.

The shape of the catalyst containing a metal oxide is not limited, and for example, it may be in the form of granules, pellets, a membrane, a sheet, a honeycomb, a ribbon, a ring, a net or a wire. When a fluid is passed through a column packed with a catalyst at the time of applying continuous contact method which will be discussed later, the catalyst is preferably in the form of granules or pellets, which is easy to be packed in a column. When the catalyst is in the form of granules, their average size is preferably from 0.1 µm to 1.0 cm, more preferably from 0.1 µm to 5.0 mm, most preferably from 0.1 µm to 1 mm. When it is in the form of pellets, their average size is preferably from 0.1 mm to 5 cm, more preferably from 0.1 mm to 1.0 cm, most preferably from 0.1 mm to 5.0 mm. When the average size is within such a range, the contact surface area is large and the permeability rate of the aqueous solution is excellent, whereby the decomposition efficiency will be good. The average size is, in accordance with the general requirements for the sieving test of JIS Z8815, defined as a value calculated in accordance with the calculation method of an average particle size of JIS Z8819-2 based on a measured value for 1 kg of sample mass sieved by the dry sieving method for a sieving time of 30 minutes.

Further, in order to reduce the column pressure when a solution passes therethrough, the catalyst is preferably in the form of pellets, further preferably in the form of porous pellets.

A preferred example of the fluorinated organic compound to be treated in the present invention may be an aqueous fluorinated compound used as, for example, a surfactant such as a dispersant for emulsion polymerization of a fluororesin or a surface treatment agent. Such a fluorinated organic compound is preferably a fluorinated organic compound represented by formula $R^f$—COOX, wherein X is any one of H, Li, Na, K or $NH_4$, $R^f$ is a $C_{3-10}$ straight-chain or branched-chain alkyl group, the alkyl group has at least one fluorine atom linked to a carbon atom, and the alkyl group may have an etheric oxygen atom between carbon atoms (in the present invention, this compound is also referred to as a fluorocarboxylic acid or its salt); or a fluorinated organic compound represented by formula $R^f$—$SO_3$X, wherein X is any one of H, Li, Na, K or $NH_4$, $R^f$ is a $C_{3-10}$ straight-chain or branched-chain alkyl group, the alkyl group has at least one fluorine atom linked to a carbon atom, and the alkyl group may have an etheric oxygen atom between carbon atoms (in the present invention, this compound is also referred to as a fluorosulfonic acid or its salt).

The following are specific examples of the fluorocarboxylic acid or its salt represented by formula $R^f$—COOX.

Specific examples of the fluorocarboxylic acid or its salt wherein X is H include $C_3F_7OCF_2CF_2OCF_2COOH$, $C_4F_9OCF_2CF_2OCF_2COOH$, $C_5F_{11}OCF_2CF_2OCF_2COOH$, $C_6F_{13}OCF_2CF_2OCF_2COOH$, $C_3F_7O(CF_2CF_2O)_2CF_2COOH$, $C_4F_9O(CF_2CF_2O)_2CF_2COOH$, $C_5F_{11}O(CF_2CF_2O)_2CF_2COOH$, $C_6F_{13}O(CF_2CF_2O)_2CF_2COOH$, $C_3F_7O(CF_2CF_2O)_3CF_2COOH$, $C_4F_9O(CF_2CF_2O)_3CF_2COOH$, $C_5F_{11}O(CF_2CF_2O)_3CF_2COOH$, $C_6F_{13}O(CF_2CF_2O)_3CF_2COOH$, $C_4F_9OCF_2CF_2OCF_2CF_2COF_2COOH$, $C_2F_5OCF_2CF_2OCF_2CF_2COF_2COOH$, $C_3F_7OCF(CF_3)CF_2OCHFCOOH$, $CF_3OCF_2OCF_2OCF_2OCF_2COOH$, $C_8F_{17}COOH$, $CF_3CF_2O(CF_2)_5COOH$, $CF_3CFHO(CF_2)_5COOH$, $CF_3OC_3F_6OCF(CF_3)COOH$, $CF_3O(CF_2)_3OCHFCF_2COOH$, $C_7F_{15}COOH$, $C_4F_9OCF(CF_3)COOH$, $C_4F_9OCF_2COOH$, $CF_3OCF_2CF_2OCF_2COOH$, $C_2F_5OCF_2CF_2OCF_2COOH$, $CF_3O(CF_2)_3OCHFCOOH$, $CF_3OCF_2OCF_2OCF_2COOH$, $C_6F_{13}COOH$, $C_4F_9OCF_2COOH$, $C_3F_7OCF_2CF_2COOH$, $C_3F_7OCHFCF_2COOH$, $CF_3CFHO(CF_2)_3COOH$, $CF_3OCF_2CF_2OCF_2COOH$, $C_5F_{11}COOH$, $C_2F_5OCF_2CF_2COOH$, $C_3F_7OCHFCOOH$, $CF_3OCF_2CF_2COOH$ and $CF_3O(CF_2CF_2O)_2CF_2COOH$.

Specific examples of the fluorocarboxylic acid or its salt wherein X is Li include $C_3F_7OCF_2CF_2OCF_2COOLi$, $C_4F_9OCF_2CF_2OCF_2COOLi$, $C_5F_{11}OCF_2CF_2OCF_2COOLi$, $C_6F_{13}OCF_2CF_2OCF_2COOLi$, $C_3F_7O(CF_2CF_2O)_2CF_2COOLi$, $C_4F_9O(CF_2CF_2O)_2CF_2COOLi$, $C_5F_{11}O(CF_2CF_2O)_2CF_2COOLi$, $C_6F_{13}O(CF_2CF_2O)_2CF_2COOLi$, $C_3F_7O(CF_2CF_2O)_3CF_2COOLi$, $C_4F_9O(CF_2CF_2O)_3CF_2COOLi$, $C_5F_{11}O(CF_2CF_2O)_3CF_2COOLi$, $C_6F_{13}O(CF_2CF_2O)_3CF_2COOLi$, $C_4F_9OCF_2CF_2OCF_2CF_2OCF_2COOLi$, $C_2F_5OCF_2CF_2OCF_2CF_2OCF_2COOLi$, $C_3F_7OCF(CF_3)CF_2OCHFCOOLi$, $CF_3OCF_2OCF_2OCF_2OCF_2COOLi$, $C_8F_{17}COOLi$, $CF_3CF_2O(CF_2)_5COOLi$, $CF_3CFHO(CF_2)_5COOLi$, $CF_3OC_3F_6OCF(CF_3)COOLi$, $CF_3O(CF_2)_3OCHFCF_2COOLi$, $C_7F_{15}COOLi$, $C_4F_9OCF(CF_3)COOLi$, $C_4F_9OCF_2CF_2COOLi$, $CF_3OCF_2CF_2OCF_2COOLi$, $C_2F_5OCF_2CF_2OCF_2COOLi$, $CF_3O(CF_2)_3OCHFCOOLi$, $CF_3OCF_2OCF_2OCF_2COOLi$, $C_6F_{13}COOLi$, $C_4F_9OCF_2COOLi$, $C_3F_7OCF_2CF_2COOLi$, $C_3F_7OCHFCF_2COOLi$, $CF_3CFHO(CF_2)_3COOLi$, $CF_3OCF_2CF_2OCF_2COOLi$, $C_5F_{11}COOLi$, $C_2F_5OCF_2CF_2COOLi$, $C_3F_7OCHFCOOLi$, $CF_3OCF_2CF_2COOLi$ and $CF_3O(CF_2CF_2O)_2CF_2COOLi$.

Specific examples of the fluorocarboxylic acid or its salt wherein X is Na include $C_3F_7OCF_2CF_2OCF_2COONa$, $C_4F_9OCF_2CF_2OCF_2COONa$, $C_5F_{11}OCF_2CF_2OCF_2COONa$, $C_6F_{13}OCF_2CF_2OCF_2COONa$, $C_3F_7O(CF_2CF_2O)_2CF_2COONa$, $C_4F_9O(CF_2CF_2O)_2CF_2COONa$, $C_5F_{11}O(CF_2CF_2O)_2CF_2COONa$, $C_6F_{13}O(CF_2CF_2O)_2CF_2COONa$, $C_3F_7O(CF_2CF_2O)_3CF_2COONa$, $C_4F_9O(CF_2CF_2O)_3CF_2COONa$, $C_5F_{11}O(CF_2CF_2O)_3CF_2COONa$, $C_6F_{13}O(CF_2CF_2O)_3CF_2COONa$, $C_4F_9OCF_2CF_2OCF_2CF_2OCF_2COONa$, $C_2F_5OCF_2CF_2OCF_2CF_2OCF_2COONa$, $C_3F_7OCF(CF_3)$ $CF_2OCHFCOONa$, $CF_3OCF_2OCF_2OCF_2OCF_2COONa$, $C_8F_{17}COONa$, $CF_3CF_2O(CF_2)_5COONa$, $CF_3CFHO(CF_2)_5COONa$, $CF_3OC_3F_6OCF(CF_3)COONa$, $CF_3O(CF_2)_3OCHFCF_2COONa$, $C_7F_{15}COONa$, $C_4F_9OCF(CF_3)COONa$, $C_4F_9OCF_2CF_2COONa$, $CF_3OCF_2CF_2OCF_2COONa$, $C_2F_5OCF_2CF_2OCF_2COONa$, $CF_3O(CF_2)_3OCHFCOONa$, $CF_3OCF_2OCF_2OCF_2COONa$, $C_6F_{13}COONa$, $C_4F_9OCF_2COONa$, $C_3F_7OCF_2CF_2COONa$, $C_3F_7OCHFCF_2COONa$, $CF_3CFHO(CF_2)_3COONa$, $CF_3OCF_2CF_2OCF_2COONa$, $C_5F_{11}COONa$, $C_2F_5OCF_2CF_2COONa$, $C_3F_7OCHFCOONa$, $CF_3OCF_2CF_2COONa$ and $CF_3O(CF_2CF_2O)_2CF_2COONa$.

Specific examples of the fluorocarboxylic acid or its salt wherein X is K include $C_3F_7OCF_2CF_2OCF_2COOK$, $C_4F_9OCF_2CF_2OCF_2COOK$, $C_5F_{11}OCF_2CF_2OCF_2COOK$, $C_6F_{13}OCF_2CF_2OCF_2COOK$, $C_3F_7O(CF_2CF_2O)_2CF_2COOK$, $C_4F_9O(CF_2CF_2O)_2CF_2COOK$, $C_5F_{11}O(CF_2CF_2O)_2CF_2COOK$, $C_6F_{13}O(CF_2CF_2O)_2CF_2COOK$, $C_3F_7O(CF_2CF_2O)_3CF_2COOK$, $C_4F_9O(CF_2CF_2O)_3CF_2COOK$, $C_5F_{11}O(CF_2CF_2O)_3CF_2COOK$, $C_6F_{13}O(CF_2CF_2O)_3CF_2COOK$, $C_4F_9OCF_2CF_2OCF_2CF_2OCF_2COOK$, $C_2F_5OCF_2CF_2OCF_2CF_2OCF_2COOK$, $C_3F_7OCF(CF_3)CF_2OCHFCOOK$, $CF_3OCF_2OCF_2OCF_2COOK$, $C_8F_{17}COOK$, $CF_3CF_2O(CF_2)_5COOK$, $CF_3CFHO(CF_2)_5COOK$, $CF_3OC_3F_6OCF(CF_3)COOK$, $CF_3O(CF_2)_3OCHFCF_2COOK$, $C_7F_{15}COOK$, $C_4F_9OCF(CF_3)COOK$, $C_4F_9OCF_2CF_2COOK$, $CF_3OCF_2CF_2OCF_2COOK$, $C_2F_5OCF_2CF_2OCF_2COOK$, $CF_3O(CF_2)_3OCHFCOOK$, $CF_3OCF_2OCF_2OCF_2COOK$, $C_6F_{13}COOK$, $C_4F_9OCF_2COOK$, $C_3F_7OCF_2CF_2COOK$, $C_3F_7OCHFCF_2COOK$, $CF_3CFHO(CF_2)_3COOK$, $CF_3OCF_2CF_2OCF_2COOK$, $C_5F_{11}COOK$, $C_2F_5OCF_2CF_2COOK$, $C_3F_7OCHFCOOK$, $CF_3OCF_2CF_2COOK$ and $CF_3O(CF_2CF_2O)_2CF_2COOK$.

Specific examples of the fluorocarboxylic acid or its salt wherein X is $NH_4$ include $C_3F_7OCF_2CF_2OCF_2COONH_4$, $C_4F_9OCF_2CF_2OCF_2COONH_4$, $C_5F_{11}OCF_2CF_2OCF_2COONH_4$, $C_6F_{13}OCF_2CF_2OCF_2COONH_4$, $C_3F_7O(CF_2CF_2O)_2CF_2COONH_4$, $C_4F_9O(CF_2CF_2O)_2CF_2COONH_4$, $C_5F_{11}O(CF_2CF_2O)_2CF_2COONH_4$, $C_6F_{13}O(CF_2CF_2O)_2CF_2COONH_4$, $C_3F_7O(CF_2CF_2O)_3CF_2COONH_4$, $C_4F_9O(CF_2CF_2O)_3CF_2COONH_4$, $C_5F_{11}O(CF_2CF_2O)_3CF_2COONH_4$, $C_6F_{13}O(CF_2CF_2O)_3CF_2COONH_4$, $C_4F_9OCF_2CF_2OCF_2CF_2OCF_2COONH_4$, $C_2F_5OCF_2CF_2OCF_2CF_2OCF_2COONH_4$, $C_3F_7OCF(CF_3)CF_2OCHFCOON_4$, $CF_3OCF_2OCF_2OCF_2COONH_4$, $C_8F_{17}COONH_4$, $CF_3CF_2O(CF_2)_5COONH_4$, $CF_3CFHO(CF_2)_5COONH_4$, $CF_3OC_3F_6OCF(CF_3)COONH_4$, $CF_3O(CF_2)_3OCHFCF_2COONH_4$, $C_7F_{15}COONH_4$, $C_4F_9OCF(CF_3)COONH_4$, $C_4F_9OCF_2CF_2COONH_4$, $CF_3OCF_2CF_2CF_2OCF_2COONH_4$, $C_2F_5OCF_2CF_2OCF_2COONH_4$, $CF_3O(CF_2)_3OCHFCOONH_4$, $CF_3OCF_2OCF_2OCF_2COONH_4$, $C_6F_{13}COONH_4$, $C_4F_9OCF_2COONH_4$, $C_3F_7OCF_2CF_2COONH_4$, $C_3F_7OCHFCF_2COONH_4$, $CF_3CFHO(CF_2)_3COONH_4$, $CF_3OCF_2CF_2OCF_2COONH_4$, $C_5F_{11}COONH_4$, $C_2F_5OCF_2CF_2COONH_4$, $C_3F_7OCHFCOONH_4$, $CF_3OCF_2CF_2COONH_4$ and $CF_3O(CF_2CF_2O)_2CF_2COONH_4$.

The following are specific examples of the fluorosulfonic acid or its salt represented by formula $R^f$—$SO_3X$.

Specific examples of the fluorosulfonic acid or its salt wherein X is H include $C_8F_{17}SO_3H$, $C_4F_9SO_3H$, $C_6F_{13}CH_2CH_2SO_3H$ and $CF_3SO_3H$.

Specific examples of the fluorosulfonic acid or its salt wherein X is Li include $C_8F_{17}SO_3Li$, $C_4F_9SO_3Li$, $C_6F_{13}CH_2CH_2SO_3Li$ and $CF_3SO_3Li$.

Specific examples of the fluorosulfonic acid or its salt wherein X is Na include $C_8F_{17}SO_3Na$, $C_4F_9SO_3Na$, $C_6F_{13}CH_2CH_2SO_3Na$ and $CF_3SO_3Na$.

Specific examples of the fluorosulfonic acid or its salt wherein X is K include $C_8F_{17}SO_3K$, $C_4F_9SO_3K$, $C_6F_{13}CH_2CH_2SO_3K$ and $CF_3SO_3K$.

Specific examples of the fluorosulfonic acid or its salt wherein X is $NH_4$ include $C_8F_{17}SO_3NH_4$, $C_4F_9SO_3NH_4$, $C_6F_{13}CH_2CH_2SO_3NH_4$ and $CF_3SO_3NH_4$.

In the present invention, the water-soluble fluorinated organic compound is preferably a fluorinated organic compound, at least 0.1 g of which is dissolved, particularly preferably at least 1 g of which is dissolved, in 100 g of water at 25° C.

In the present invention, the concentration of the fluorinated organic compound in the aqueous solution is preferably normally from 1 mass ppm to 30 mass %, more preferably 1 mass ppm to 10 mass %, most preferably from 1 mass ppm to 1 mass %. The pH of the aqueous solution of the fluorinated organic compound is preferably from 3 to 14.

The amount of the catalyst containing a metal oxide, which the fluorinated organic compound contacts with is preferably from 0.01 to 1,000 times, particularly preferably from 0.1 to 100 times the mass of the fluorinated organic compound.

As contact methods for the aqueous solution of a fluorinated organic compound and the catalyst, both batch contact method and continuous contact method may be employed.

When the batch contact method is applied, a catalyst and an aqueous solution of a fluorinated organic compound are put into a reactor; they are mixed with stirring in order to be efficiently and uniformly contacted with each other, so that the fluorinated organic compound is sufficiently decomposed; and then the catalyst is separated from the aqueous solution by filtration. The contact time of the aqueous solution of the fluorinated organic compound with the catalyst is preferably from 1 minute to 5 hours, more preferably from 10 minutes to 5 hours.

When the continuous contact method is applied, an aqueous solution of a fluorinated organic compound is passed through a column packed with a catalyst so that it is contacted with the catalyst. The length and diameter of the column and the flow rate are not specifically limited; however, the contact time with the catalyst is preferably from 1 minute to 5 hours, more preferably from 10 minutes to 5 hours.

Usually, the column length is preferably from 10 cm to 10 m, and the column diameter is preferably from 1 cm to 1 m.

The flow rate is preferably from 1 g/hr to 10 t/hr, more preferably from 1 g/hr to 5 t/h r.

From an industrial viewpoint, the continuous contact method wherein a solution is passed through a catalyst packed in a column is more efficient in processing than the batch contact, and so it is preferred.

The contact temperature of the fluorinated organic compound and the catalyst is preferably within the range of from 0 to 100° C., more preferably from 10° C. to 60° C., most preferably from 20 to 50° C.

In the present invention, in order to prevent environmental pollution, the aqueous solution of the fluorinated organic compound is contacted with a catalyst containing a metal oxide, whereby at least 98.5%, or particularly at least 99.5% of the fluorinated organic compound in the aqueous solution can be decomposed.

EXAMPLES

Now, the present invention will be described in more detail with reference to Examples. It should be understood, however, that the present invention is by no means limited to these Examples.

Example 1

1,000 g of an aqueous solution (pH=6) containing 800 mass ppm of $C_7F_{15}COONH_4$ (hereinafter referred to as APFO) was passed through a transparent acrylic cylindrical column (column length: 15 cm, column diameter: 2 cm) packed with 40 g of a metal oxide catalyst comprising nickel oxide and aluminum oxide wherein their mass ratio nickel oxide/aluminum oxide is from 0.19 to 0.21 (manufactured by Johnson Matthey, ACCENT™ 81-1T, average particle size: 1.2 mm) at a flow rate of 100 g/hr at 40° C. The contact time between the fluorinated composition and the catalyst was about 30 minutes.

A calibration curve was obtained from the peak area obtained from measurement of aqueous solutions containing APFO having known concentrations by using liquid chromatography-mass spectrometry (LC-MS), and APFO content in the aqueous solution was calculated from the measured peak area of the sample solution after the solution was passed through the column by applying it to the calibration curve.

As a result, APFO content in the solution after it was passed through the column was 3.0 mass ppm. Further, APFO was not detected from the extract of 40 g of the metal oxide catalyst after the solution was passed through the column to which 5 g of hydrochloric acid and 200 g of methanol were added, which was extracted for 2 hours at room temperature. Therefore, APFO in the aqueous solution of the fluorinated organic compound after the contact with the catalyst was not considered to be removed by absorption of the catalyst, but it was considered to be chemically decomposed to low molecules.

Example 2

In the same manner as in Example 1 except that an aqueous solution (pH=6) containing $CF_3CF_2OCF_2CF_2OCF_2COONH_4$ (hereinafter referred to as EEA) as a fluorinated organic compound, the aqueous solution containing the fluorinated organic compound was passed through the column packed with the catalyst at a flow rate of 100 g/hr (contact time with the catalyst was about 30 minutes) at 40° C., and the concentration of EEA after the solution was passed through the column was measured.

As a result, EEA content in the solution after it was passed through the column was 9.2 mass ppm. Further, EEA was not detected from the extract of 40 g of the metal oxide catalyst after the solution was passed through the column to which 5 g of hydrochloric acid and 200 g of methanol were added, which was extracted for 2 hours at room temperature. Therefore, EEA in the aqueous solution of the fluorinated organic compound after the contact with the catalyst was not considered to be removed by absorption of the catalyst, but it was considered to be chemically decomposed to low molecules.

Example 3

In the same manner as in Example 1 except that an aqueous solution containing 800 mass ppm of APFO which was adjusted to have a pH of 13 by adding sodium hydroxide was used, the aqueous solution containing the fluorinated organic compound was passed through the column packed with the catalyst at a flow rate of 100 g/hr (contact time with the catalyst was about 30 minutes) at 40° C., and the concentration of APFO after the solution was passed through the column was measured.

As a result, APFO content in the solution after it was passed through the column was 5.0 mass ppm. Further, APFO was not detected from the extract of 40 g of the metal oxide catalyst after the solution was passed through the column to which 5 g of hydrochloric acid and 200 g of methanol were added, which was extracted for 2 hours at room temperature. Therefore, APFO in the aqueous solution of the fluorinated organic compound after the contact with the catalyst was not considered to be removed by absorption of the catalyst, but it was considered to be chemically decomposed to low molecules.

Example 4

In the same manner as in Example 2 except that an aqueous solution containing 800 mass ppm of EEA which was adjusted to have a pH of 13 by adding sodium hydroxide was used, the aqueous solution containing the fluorinated organic compound was passed through the column packed with the catalyst at a flow rate of 100 g/hr (contact time with the catalyst was about 30 minutes) at 40° C., and the concentration of APFO after the solution was passed through the column was measured.

As a result, EEA content in the solution after it was passed through the column was 10.5 mass ppm. Further, EEA was not detected from the extract of 40 g of the metal oxide catalyst after the solution was passed through the column to which 5 g of hydrochloric acid and 200 g of methanol were added, which was extracted for 2 hours at room temperature. Therefore, EEA in the aqueous solution of the fluorinated organic compound after the contact with the catalyst was not considered to be removed by absorption of the catalyst, but it was considered to be chemically decomposed to low molecules.

From the above Examples 1 to 4, it was found that an aqueous solution containing a fluorinated organic compound is contacted with a catalyst containing a metal oxide, whereby the fluorinated organic compound in the aqueous solution can be decomposed. This is an unexpected function effect from a technical common knowledge such that a water-soluble fluorinated organic compound used as a surfactant or a surface treatment agent is especially hardly decomposable.

INDUSTRIAL APPLICABILITY

By the decomposition method of the present invention, a hardly-decomposable water-soluble fluorinated organic compound used as a surfactant or a surface treatment agent can be easily decomposed. Therefore, the method of the present invention is effective for the prevention of the environment pollution by hardly decomposable fluorinated organic compounds.

The entire disclosure of Japanese Patent Application No. 2008-057381 filed on Mar. 7, 2008 including specification, claims and summary is incorporated herein by reference in its entirety.

What is claimed is:
1. A method for decomposing a fluorinated organic compound, comprising contacting an aqueous solution containing a water-soluble fluorinated organic compound with a catalyst comprising nickel oxide, wherein the aqueous solution con- taining the fluorinated organic compound is contacted with the catalyst at a temperature of from 0° C. to 100° C.

2. The method for decomposing a fluorinated organic compound according to claim 1, wherein the catalyst further comprises, as a carrier component, at least one member selected from the group consisting of aluminum oxide, zeolite, zinc oxide, lanthanum oxide, silica, magnesium oxide, calcium oxide and titanium oxide.

3. The method for decomposing a fluorinated organic compound according to claim 2, wherein the catalyst comprises nickel oxide and aluminum oxide, and their mass ratio (nickel oxide/aluminum oxide) is from 0.01 to 100.

4. The method for decomposing a fluorinated organic compound according to claim 1, wherein the catalyst is in the form of granules and their average size is from 0.1 μm to 1.0 cm.

5. The method for decomposing a fluorinated organic compound according to claim 1, wherein the catalyst is in the form of pellets and their average size is from 0.1 mm to 5 cm.

6. The method for decomposing a fluorinated organic compound according to claim 1, wherein the aqueous solution containing a water-soluble fluorinated organic composition is passed through a column packed with the catalyst.

7. The method for decomposing a fluorinated organic compound according to claim 1, wherein the fluorinated organic compound is a fluorocarboxylic acid, a fluorosulfonic acid or a salt thereof.

8. The method for decomposing a fluorinated organic compound according to claim 1, wherein the concentration of the fluorinated organic compound in the aqueous solution is within a range of from 1 mass ppm to 30 mass %.

9. The method for decomposing a fluorinated organic compound according to claim 1, wherein the amount of the catalyst is from 0.01 to 1,000 times the mass of the fluorinated organic compound in the aqueous solution containing the fluorinated organic compound.

10. The method for decomposing a fluorinated organic compound according to claim 1, wherein the aqueous solution containing a water-soluble fluorinated organic compound is contacted with the catalyst for a contact time of from 1 minute to 5 hours.

11. The method according to claim 1, wherein the water-soluble fluorinated organic compound comprises a compound of the formula $R^f$—COOX, wherein X is H, Li, Na, K or $NH_4$ and $R^f$ is a $C_{3-10}$ straight chain or branched chain alkyl group, wherein the alky group has at least one fluorine atom between carbon atoms.

12. The method according to claim 1, the water-soluble fluorinated organic compound comprises a compound of the formula $R^f$—$SO_3$X, wherein X is H, Li, Na, K or $NH_4$, $R^f$ is a $C_{3-10}$ straight-chain or branched-chain alkyl group, wherein the alkyl group has at least one fluorine atom linked to a carbon atom, and the alkyl group optionally has an etheric oxygen atom between carbon atoms.

* * * * *